United States Patent [19]

Jackson et al.

[11] Patent Number: 4,741,944
[45] Date of Patent: May 3, 1988

[54] WET WIPE AND WIPE DISPENSING ARRANGEMENT

[75] Inventors: David M. Jackson, Roswell, Ga.; William H. Vogler, Neenah, Wis.

[73] Assignee: Kimberly-Clark Corporation, Neenah, Wis.

[21] Appl. No.: 891,716

[22] Filed: Jul. 30, 1986

[51] Int. Cl.$^4$ .............................................. D06N 7/04
[52] U.S. Cl. ................................. 428/152; 15/104.93; 428/171; 428/284; 428/286; 428/297; 428/298; 428/340; 428/903; 428/905; 428/913; 604/359
[58] Field of Search ............... 428/152, 171, 172, 198, 428/219, 284, 286, 296, 298, 903, 905, 913, 297, 340; 604/358, 359, 360; 15/104.93

[56] References Cited

U.S. PATENT DOCUMENTS

| 2,957,512 | 10/1960 | Wade | 428/152 |
| 3,316,136 | 4/1967 | Pufahl | 428/152 |
| 3,644,157 | 2/1972 | Draper | 156/160 |
| 3,687,797 | 8/1972 | Wideman | 156/85 |
| 3,849,241 | 11/1974 | Butin et al. | 264/211 |
| 4,355,425 | 10/1982 | Jones et al. | 2/402 |
| 4,418,123 | 11/1983 | Bunnelle et al. | 428/517 |
| 4,436,780 | 3/1984 | Hotchkiss et al. | 428/198 |
| 4,543,099 | 9/1985 | Bunnelle et al. | 428/152 |
| 4,555,811 | 12/1985 | Shimalla | 428/903 |
| 4,600,620 | 7/1986 | Lloyd et al. | 428/913 |
| 4,606,964 | 8/1986 | Wideman | 428/152 |
| 4,657,802 | 4/1987 | Morman | 604/358 |
| 4,692,368 | 9/1987 | Taylor et al. | 428/152 |

OTHER PUBLICATIONS

U.S. patent appliction Ser. No. 06/843,428 to D. H. DaPonte Filed on Mar. 24, 1986, entitled "Composite Elastomeric Material and Process for Making the Same".

Primary Examiner—James J. Bell
Attorney, Agent, or Firm—Joseph P. Harps

[57] ABSTRACT

A wet wipe which is elastic in at least one direction, and includes an elastic sheet having at least one non-elastic non-woven web joined thereto at least at two areas. The non-elastic web is gathered between said two areas and a liquid is distributed within the sheet and/or the web. The sheet is preferably a nonwoven web of meltblown ethylene vinyl acetate fibers and the non-elastic web is preferably a nonwoven web of spunbonded fibers. The liquid may include a fragrance and/or a preservative. An arrangement for dispensing an interleaved stack of the wet wipes is also provided.

15 Claims, 2 Drawing Sheets

WET WIPE AND WIPE DISPENSING ARRANGEMENT

FIELD OF THE INVENTION

The present invention falls within the field of wipes, for example, disposable wet wipes which may be utilized for purposes of infant hygiene. Also included within the field of the present invention are dispensing arrangements for wipes.

BACKGROUND OF THE INVENTION

The advent of formation of plastic materials such as plastic sheets, films and nonwoven webs by extrusion processes such as, for example, slot film extrusion, blown bubble film extrusion, meltblowing of nonwoven webs and spinbonding of nonwoven webs allowed a wide variety of products to be manufactured so inexpensively that they could be viewed as disposable, as opposed to reusable. Representatives of such disposable products include disposable diapers, disposable tissues and disposable wipes, for example, disposable wet wipes.

A problem which has confronted those in the art is the formation of a wipe which may be easily dispensed by the consumer. A particularly troublesome area has been the dispensation of disposable wet wipes which are designed to be utilized by a mother in maintaining proper infant hygiene. Wipes of this sort should preferably be easily and readily dispensable because, in many situations where need for wipe dispensation occurs, the mother or other individual who is caring for the infant is holding or otherwise attempting to control the infant. As those who have encountered such a situation will rapidly admit, the situation demands the utmost patience on the part of the mother. In such a situation, the necessity of having to deal with wipes that will not immediately and easily dispense in one-at-a-time fashion can be quite frustrating. Unfortunately, the very nature of a wet wipe makes the wipe difficult to dispense in one-at-a-time fashion.

The difficulty in one-at-a-time dispensation of wet wipes arises from the fact that the wipes tend to cling to each other within their dispenser. This problem is very apparent in the present infant hygiene wet wipe dispensing systems where the wipes are stacked, in planar form, one on top of each other within a container that is designed to retain the liquid saturated wipes. Upon opening of the container, the user is confronted with a stack of generally coinciding wipes which characteristically cling to each other due to the presence of the liquid retained within the stack of wipes. In such a situation, the user usually has to carefully peel the top wipe off of the stack starting at the edge. This is a tedious and thus undesirable operation. Those in the art have attempted to overcome this problem by providing a wipe dispensing system where the individual wipes are connected along a serrated edge. In this system, dispensation involves withdrawing approximately a wipe and a half from the container and applying a jerking motion to the leading wipe to disconnect the leading wipe from the remainder of the wipes which, with the exception of the leading portion of the now leading wipe, remain within the container. Unfortunately, the jerking motion does not always result in a parting of the serrations interconnecting the wipes, and thus user time and aggravation are still present.

Yet another problem which is associated with the prior wet wipes is that, over time, the liquid which has been applied to the wipes tends, under the influence of gravity, to seep down to the bottom of the container. Thus, the topmost or leading wipe is usually the driest of all of the wipes to be dispensed. This, of course, is quite unsatisfactory.

DEFINITIONS

The term "elastic" is used herein to mean any material which, upon application of a biasing force, is stretchable, that is, elongatable, to a stretched, biased length which is at least about 125 percent, that is about one and one quarter, of its relaxed, unbiased length, and which, will recover at least 40 percent of its elongation upon release of the stretching, elongating force. A hypothetical example which would satisfy this definition of an elastic material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, for example, 100 percent or more, and many of these will recover to substantially their original relaxed length, for example, to within 105 percent of their original relaxed length, upon release of the stretching, elongating force.

As used herein, the term "non-elastic" refers to any material which does not fall within the definition of "elastic," above.

As used herein the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein the term "nonwoven web" means a web of material which has been formed without use of weaving processes which produce a structure of individual fibers or threads which are interwoven in an identifiable repeating manner. Nonwoven webs have been, in the past, formed by a variety of processes such as, for example, meltblowing processes, spinbonding processes, film aperturing processes and staple fiber carding processes.

As used herein the term "meltblown microfibers" means small diameter fibers having an average diameter not greater than about 100 microns, preferably having a diameter of from about 0.5 microns to about 50 microns, more preferably having an average diameter of from about 4 microns to about 40 microns and which are made by extruding a molten thermoplastic material through a plurality of fine, usually circular, die capillaries as molten threads or filaments into a high velocity gas (e.g. air) stream which attenuates the filaments of molten thermoplastic material to reduce their diameter to the range stated above. Thereafter, the meltblown microfibers are carried by the high velocity gas stream and are deposited on a collecting surface to form a web of randomly disbursed meltblown microfibers. Such a process is disclosed, for example, in U.S. Pat. No.

3,849,241 to Butin and the disclosure of this patent is hereby incorporated by reference.

As used herein the term "spunbonded microfibers" means small diameter fibers having a diameter not greater than about 100 microns, preferably having a diameter of from about 10 microns to about 50 microns, more preferably having a diameter of from about 12 microns to about 30 microns and which are made by extruding a molten thermoplastic material as filaments through a plurality of fine, usually circular, capillaries of a spinnerette with the diameter of the extruded filaments then being rapidly reduced as by, for example, eductive drawing or other well known spinbonding mechanisms. The production of spunbonded nonwoven webs is illustrated in U.S. Pat. No. 4,340,563 to Appel and the disclosure of this patent is hereby incorporated by reference.

As used herein the term "sheet" means a layer which may be either a film or a nonwoven web.

As used herein, the term "wet wipe" refers to a wipe which, during its manufacture, has a liquid applied thereto so that the liquid will be retained within the wipe until its utilization by a consumer. The liquid may include a fragrance and/or an emollient and may serve to aid the wipe in retention of materials which are to be wiped up during its utilization.

As used herein, the term "stretch-bonded laminate" refers to a material having at least two layers of nonwoven webs and/or films with at least one of the layers of nonwoven webs and/or films being elastic and at least one of the layers of the nonwoven webs and/or films being non-elastic. The elastic nonwoven web or film layer is joined to the non-elastic nonwoven web or film layer at intermittent joining points or areas while the nonwoven webs and/or films are in juxtaposed configuration and while the elastic nonwoven web or film has a tensioning force applied thereto in order to bring the elastic nonwoven web or film to a stretched condition. Upon removal of the tensioning force after joining of the webs and/or films, the elastic nonwoven web or film will attempt to recover to its unstretched condition and will thereby gather the non-elastic nonwoven web or film between the points or areas of joining of the two layers. The composite material is elastic in the direction of stretching of the elastic layer during joining of the layers and may be stretched until the gathers of the non-elastic nonwoven web or film layer have been removed. A stretch-bonded laminate may include more than two layers. For example, the elastic nonwoven web or film may have a non-elastic nonwoven web or film joined to both of its sides while it is in a stretched condition so that a three layer nonwoven web or film composite is formed having the structure of—gathered non-elastic (nonwoven web or film) /elastic (nonwoven web or film)/gathered non-elastic (nonwoven web or film). Yet other combinations of elastic and non-elastic layers may be utilized.

As used herein the term "palindromic" means a multi-layer laminate, for example a stretch-bonded laminate, which is substantially symmetrical. Examples of palindromic laminates would have layer configurations of A/B/A, A/B/B/A, A/A/B/B/A/A, A/B/C/B/A, etc. Examples of non-palindromic layer configurations would include A/B/C, A/B/C/A, A/B/C/D, etc.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solid solvents, particulates and materials added to enhance processability of the composition.

OBJECTS OF THE INVENTION

Accordingly, it is an object of the present invention to provide a wipe which may be easily and immediately dispensed.

Another object of the present invention is to provide a disposable wipe which may be easily and immediately dispensed.

Yet another object of the present invention is to provide a disposable wet wipe which may be easily and immediately dispensed.

An even further object of the present invention is to provide a disposable wet wipe which may be easily and immediately dispensed where the liquid retained in a group of stacked wipes does not readily seep to the bottom of the stack of wipes under the influence of gravity.

A further object of the present invention is to provide a dispensing system for disposable wet wipes where the wipes may be easily and immediately dispensed because the wipes are interleaved in a manner so as to aid in their dispensation from their container and where the liquid retained within the stack of wipes within the container does not readily seep to the bottom of the stack under the influence of gravity.

Still further objects and the broad scope of applicability of the present invention will become apparent to those of skill in the art from the details given hereinafter. However, it should be understood that the detailed description of the presently preferred embodiment of the present invention is given herein only by way of illustration because various changes and modifications well within the spirit and scope of the invention will become apparent to those of skill in the art in view of this detailed description.

SUMMARY OF THE INVENTION

In response to the above-discussed problems the present invention provides a wet wipe which is elastic in at least one direction and which includes an elastic sheet and at least one non-elastic, non-woven web joined to the elastic sheet at least at two areas, the non-elastic web being gathered between the two areas. Additionally, a liquid is distributed within the sheet and/or the web. The liquid includes at least one material selected from the group including preservatives, fragrances, emollients, humectants, detergents and soaps.

Preferably the elastic sheet is an elastic non-woven web of meltblown fibers, for example meltblown microfibers, and the non-elastic web is a web of spunbonded fibers, for example spunbonded microfibers, with the meltblown fibers being formed from an ethylene vinyl acetate copolymer having from about 10 percent, by weight, to about 50 percent, by weight, of vinyl acetate monomer and the spunbonded fibers being formed from a polypropylene having a polydispersity of from about 1 to about 5. The basis weight of the spunbonded polypropylene web, in ungathered condition, may vary from about 10 grams per square meter to about 30 grams per square meter while the basis weight of the relaxed elastic meltblown nonwoven web may vary from about 30 grams per square meter to about 50 grams per square meter. Even more particularly, the polypropylene preferably may have a melt flow of about 35 grams per 10 minutes when measured in accordance with ASTM D 1238 at 230 degrees C. and under a 2,160 gram load, the ethylene vinyl acetate copolymer may have about 28 percent, by weight, of vinyl acetate monomer and a melt flow of about 180 grams per 10 minutes when measured in accordance with ASTM D 1238 at 190 degrees C. and under a 2,160 gram load.

In one embodiment the wet wet wipe is a palindromic stretch-bonded wet wipe which is elastic in at least one direction and which is adapted to stretch from at least about 30 percent to about 50 percent. This preferred wet wipe includes an inner elastic nonwoven web having a relaxed basis weight of from about 35 grams per square meter to about 40 grams per square meter with the elastic web being formed from meltblown microfibers of an ethylene vinyl acetate copolymer having about 28 percent, by weight, of vinyl acetate monomer and a melt flow rate of about 180 grams per 10 minutes when measured in accordance with ASTM D 1238 at 190 degrees C. and under a 2,160 gram load. Also included in this preferred wet wipe are two outer non-elastic nonwoven webs, each having an ungathered basis weight of from about 10 grams per square meter to about 20 grams per square meter with the non-elastic webs being formed from spunbonded microfibers of a polypropylene having a polydispersity of about 4.5 and a melt flow rate of about 35 grams per 10 minutes when measured in accordance with ASTM D 1238 at 230 degrees C. and under a 2,160 gram load and from about 80 percent, by weight, to about 160 percent, by weight, for example from about 110 percent, by weight, to about 130 percent, by weight, based on the combined weight of the elastic and non-elastic webs, of a liquid including at least one material selected from the group including fragrances, preservatives, soaps, detergents, humectants and emollients.

In a preferred embodiment the stretch-bonded palindromic wipe is adapted to stretch about 40 percent, the meltblown web of ethylene vinyl acetate copolymer is adapted, in unjoined condition, to stretch about 100 percent and has a relaxed basis weight of about 37 grams per square meter, the two non-elastic webs are bonded to the elastic web by thermal pin embossment and each have an ungathered basis weight of about 12.5 grams per square meter, the liquid is about 120 percent, by weight, based on the combined weight of the elastic and non-elastic webs, and includes about 94.475 percent, by weight, of water; about 0.20 percent, by weight, of benzalkonium chloride; about 0.10 percent, by weight, of citric acid; about 0.60 percent, by weight, of disodium phosphate; about 0.10 percent, by weight, of trisodium ethylene diamine tetraacetic acid; about 1.20 percent, by weight, of polyethylene glycol-75 lanolin; about 0.50 percent, by weight, of cocoamphocarboxyglycinate; about 2.00 percent, by weight, of propylene glycol; about 0.10 percent, by weight, of methylparaben; about 0.05 percent, by weight, of propylparaben; about 0.05 percent, by weight, of butylparaben; about 0.825 percent, by weight, of polysorbate 20 and about 0.45 percent, by weight, of a fragrance.

The invention is also directed to an arrangement for individually dispensing wipes where each wipe has a plurality of generally parallel gathers on at least one surface thereof. The arrangement includes a container adapted to define a dispensing orifice and a stack of wipes located within the container and interleaved so that the gathers of adjacent interleaved wipes are in general facing parallel alignment to each other so that the gathers of a leading wipe are adapted to temporarily engage the gathers of an immediately following wipe upon removal of the leading wipe from the container through the dispensing orifice and effect partial removal of the following wipe from the container by way of the orifice. Preferably, the wipes are elastic and are arranged within the container so that, upon removal of a leading wipe from said container through said orifice, the direction of elasticity of the wipe is generally the same as an idealized direction of removal of the wipe from the container. This arrangement allows the wipes to stretch upon being removed from the container so that the removed wipe snaps into the user's hand to give a positive indication of removal. The wipes of the present invention are preferably utilized in the dispensing arrangement.

DESCRIPTION OF THE PREFERRED EMBODIMENT

Figure 1:
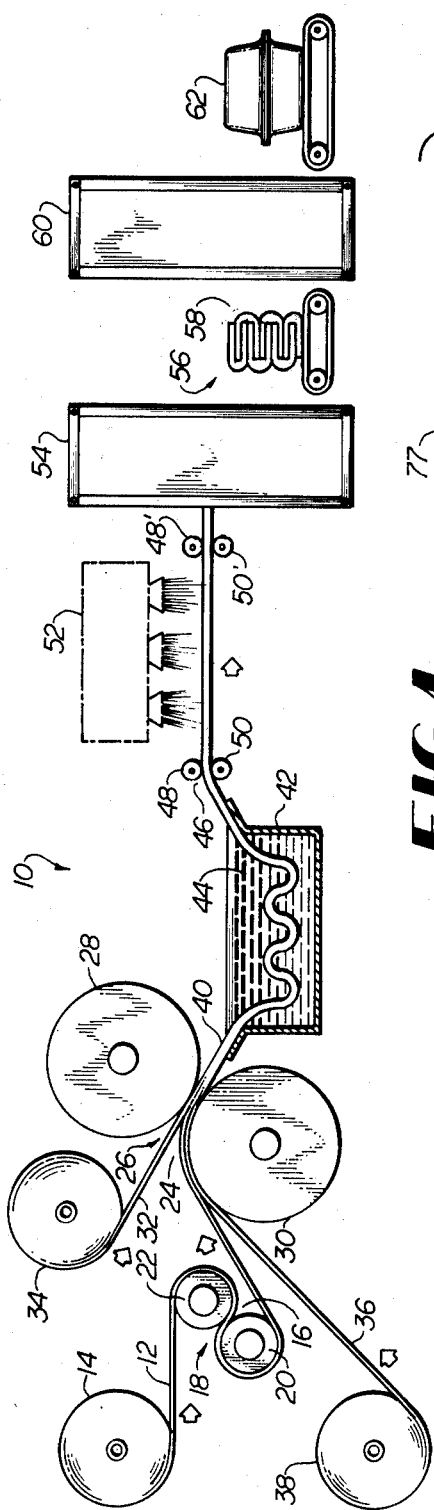
FIG. 1 is a schematic representation of a process for forming the wipes of the present invention.

Referring now to the drawings where like reference numbers represent like or equivalent structure and, in particular, to FIG. 1, there is schematically illustrated at 10 a process for forming stretch-bonded wet wipes by heat-bonding a non-elastic web to each of the two opposite sides of an elastic sheet which may be an elastic film or an elastic non-woven web. A preferred elastic sheet 12 is an elastic meltblown nonwoven web of coherent microfibers formed from a copolymer of ethylene with at least one other vinyl monomer selected from the group consisting of vinyl ester monomers and unsaturated aliphatic monocarboxylic acids and alkyl esters of these monocarboxylic acids. Exemplary copolymers are those of ethylene with vinyl acetate (EVA) having a melt flow in the range of from about 32 to 500 grams per 10 minutes when measured in accordance with ASTM D 1238 at 190 degrees C. and under a 2,160 gram load (ASTM D 1238, condition F). Such copolymers contain from about 10 percent, by weight, to about 50 percent, by weight, of vinyl acetate monomer, for example from about 18 percent, by weight, to about 36 percent, by weight, of vinyl acetate monomer and more particularly from about 26 percent, by weight, to about 30 percent, by weight, of vinyl acetate monomer. One such material may be obtained from Exxon under the trade designation Escorene LD 764 or 077.004. This EVA copolymer has about 28 percent, by weight, of vinyl acetate monomer and a melt flow of about 180 grams per 10 minutes when measured in accordance with ASTM D 1238 at 190 degrees C. and under a 2,160 gram load.

The copolymer, preferably a copolymer of ethylene and vinyl acetate, may be formed into a mixture with another polymeric material, to produce an extrudable blend that can be meltblown to form microfibers of desired properties and characteristics. Thus, an extrudable composition can be prepared from at least about 10 percent, by weight, to about 95 percent, by weight, of a copolymer of ethylene and at least one other vinyl monomer selected from the group including vinyl ester monomers, unsaturated aliphatic monocarboxylic acids, and alkyl esters of these monocarboxylic acids. The modifying polymer is a compatible polymer, preferably one formed from a monomer having olefinic unsaturation, used in an amount greater than 0 percent, by weight, up to about 90 percent, by weight, of the meltblown fibers. Exemplary modifying materials include polymers of ethylene, propylene, butene, styrene, and copolymers and compatible mixtures of these polymers and copolymers, and ABA' block copolymers, where A and A' are each a thermoplastic endblock that includes a styrenic moiety and where B is either an elastomeric poly(ethylene-butene) midblock or an elastomeric polyisoprene midblock.

If a blend is utilized the blend usually includes from at least about 10 percent, by weight, to about 95 percent, by weight, of the ethylene copolymer such as poly(ethylene-vinyl) acetate (EVA), and from at least about 5 percent, by weight, to about 90 percent, by weight, of the polyolefin. For example, the blend may include from about 40 percent, by weight, to about 90 percent, by weight, of the copolymer and from about 10 percent, by weight, to about 60 percent, by weight, of the polyolefin. Preferably, the blend includes from about 50 percent, by weight, to about 90 percent, by weight, of the copolymer and from about 10 percent, by weight, to about 50 percent, by weight, of the polyolefin. For example, the blend may include from about 50 percent, by weight, to about 80 percent, by weight, of the copolymer and from about 20 percent, by weight, to about 50 percent, by weight, of the polyolefin. One preferred blend includes about 60 percent, by weight, of the copolymer and about 40 percent, by weight, of the polyolefin.

The elastic sheet 12 may be unwound from a supply roll 14 of the elastic sheet material. The sheet 12 then travels in the direction indicated by the arrows associated therewith and passes through the nip 16 of the S roll arrangement 18 formed by the stacked rollers 20 and 22. Alternatively, the sheet 12 may be formed by known extrusion processes and passed directly through the nip 16 without being first stored on the supply roll 14. The sheet 12 passes through the nip 16 in a reverse-S path as indicated by the rotation direction arrows associated with the stacked rollers 20 and 22. From the S roll arrangement 18 the sheet 12 passes through the pressure nip 24 formed by a bonder roller arrangement 26. The bonder roller arrangement 26 includes a patterned calender embossing roller 28, for example a thermal pin embossing roller, and a smooth anvil roller 30.

A first non-elastic web 32 is unwound from a supply roll 34 and a second non-elastic web 36 is unrolled from a supply roll 38. The non-elastic nonwoven webs 32 and 36 are preferably formed from spunbonded microfibers. Exemplary materials for use in forming the non-elastic webs 32 and 36 are polyester materials, polyolefin materials or blends of one or more polyester materials with one or more polyolefin materials. An exemplary polyester fiber-forming material is polyethylene terephthalate. An exemplary fiber-forming polyolefin material is polypropylene. Of these materials polypropylene materials are preferred and preferred polypropylene material may be obtained under the trade designation PC 973 from the Himont Company, DX 5A09 from the Shell Chemical Company and 3125 from Exxon. These three materials are substantially equivalent for purposes of the present invention.

Typical characteristics of the Himont PC-973 polypropylene stated by Himont are a density of about 0.900 grams per cubic centimeter, measured in accordance with ASTM D 792; a melt flow rate obtained in accordance with ASTM D 1238, condition L, of 35 grams per ten (10) minutes; tensile of about 4,300 pounds per square inch (psi) measured in accordance with ASTM D 638; flex modulus of about 182,000 psi measured in accordance with ASTM D 790, B and a Rockwell hardness, R scale, of 93 measured in accordance with ASTM D 785 A. The PC-973 is believed to have a number average molecular weight (Mn) of about 40,100; a weight average molecular weight (Mw) of about 172,000 and a Z average molecular weight of about 674,000. The polydispersity (Mw/Mn) of the PC-973 is about 4.29.

The first non-elastic web 32 and the second non-elastic web 36 travel in the directions indicated by the arrows associated respectively therewith as supply rolls 34 and 38 rotate in the directions indicated by the respective arrows associated therewith. Both of the non-elastic webs 32 and 36 are directed to pass through the pressure nip 24 of the bonder roller arrangement 26 on the two opposite sides of the elastic sheet 12 as illustrated in FIG. 1. By virtue of the fact that the peripheral linear speed of the rollers 20 and 22 of the S roll arrangement 18 is controlled to be less than the peripheral linear speed of the rollers 28 and 30 of the bonder roll arrangement 26, the sheet 12 is stretched to a selected percent elongation and maintained in such stretched condition during bonding of the non-elastic webs 32 and 36 to the sheet 12 during their passage through the bonder roller arrangement 26. The degree of stretching of the elastic sheet 12 between the S roller arrangement 18 and the bonder roller arrangement 26 may be varied to effect different degrees of elongation (elasticity) of the stretch-bonded laminate formed upon bonding of the non-elastic webs 32 and 36 to the elastic sheet 12. In practice it has been found that an elastic stretch-bonded laminate having the ability to stretch at least 25 percent is desirable. For example, an elastic stretch-bonded laminate which is able to stretch from about 30 percent to about 50 percent is desirable. More particularly, an elastic stretch-bonded laminate which is able to stretch about 40 percent is more desirable. In order to form a stretch-bonded laminate having the above degrees of elasticity, it is necessary for the elastic sheet 12 to be stretched to a significantly greater degree upon bonding of the non-elastic webs 32 and 36 thereto. In this regard it has been generally found that the elastic sheet 12 should, upon bonding of the non-elastic webs 32 and 36 thereto, be stretched approximately 2.5 times the degree of desired elasticity in the stretch-bonded laminate. Thus, if a stretch-bonded laminate having 40 percent elasticity is desired, the elastic sheet 2 should be stretched about 100 percent.

While many bonding methods may be possible, a preferred method of bonding is by thermal bonding and, in particular, by thermal pin embossment where one or both of the patterned embossing calender roller 28 and the smooth anvil roller 30 are heated and the pressure between these two rollers is adjusted by well-known means to provide the desired temperature and bonding pressure to bond the webs 32 and 36 to the sheet 12 and thereby form a composite stretch-bonded elastic material 40. In thermal pin embossment bonding, the webs 32 and 36 are bound to the elastic sheet 12 by the action of lands or pins (not shown) which protrude from the calender roller 28 and cooperate with the anvil roller 30 to apply heat and pressure to selected intermittent areas of the three materials 12, 32 and 36 as they pass through the nip 24. This serves to bond them together.

The elastic sheet 12 of the composite elastic material 40, upon emergence of the composite material 40 from the pressure nip 24 of the bonder roll arrangement 26, is immediately relaxed and quickly recovers and gathers the non-elastic webs 32 and 36 between the intermittent bond areas formed by the bonder roller arrangement 26. Because the direction of stretching of the elastic sheet 12 is generally the same as the direction of travel of the three materials 12, 32 and 36 the generally parallel gathers in the non-elastic webs 32 and 36 will be generally perpendicular to the direction of travel of the composite material 40. Thereafter the composite elastic material 40 passes to a holding box 42 where it is maintained in a relaxed, unstretched condition for a length of time for the elastic sheet 12 to cool sufficiently to avoid its cooling while it is in a stretched condition and thereby losing all or a considerable proportion of its ability to contract from the stretched dimensions which it had assumed during bonding.

If the composite elastic material 40 is to be formed into a wet wipe, the holding box 42 may also serve as an arrangement to apply a liquid 44 to the composite elastic material 40. General types of liquids which may be applied by passage of the composite elastic material 40 through the holding box 42 include soaps, detergents, preservatives, humectants, emollients and/or fragrances. Preferred preservatives include citric acid, benzalkonium chloride, which is available from Onyx under the trade designation BTC 50, methylparaben, propylparaben and butylparaben, all three available from Costec under the respective trade designations of Cosept M, Cosept P and Cosept B. Preferred soaps include polyethylene glycol-75 lanolin, available from Emery under the trade designation ethoxylan 1686/50%, and polysorbate 20, available from Heterene under the trade designation Hetsorb L20. A preferred humectant is propylene glycol, available from Fisher under the trade designation 1,2-propanediol. A preferred emollient is cocoamphocarboxyglycinate, available from Miranol under the trade designation Miranol C2M. A preferred fragrance is "clean baby", available from Hercules, Inc. under the trade designation SL 84-899. A particularly preferred liquid to be applied to the elastic composite material 40 is formed by initially forming four separate solutions and then blending them together. These four solutions are detailed below in Table I:

TABLE I

| SOLUTION | COMPONENT | WEIGHT PERCENT (As a Percent of the Final Solution) |
|---|---|---|
| 1 | water | 34.475 |
| 1 | benzalkonium chloride | 0.20 |
| 1 | citric acid | 0.10 |
| 1 | disodium phosphate (an emulsifier and buffer) | 0.60 |
| 1 | trisodium ethylene-diamine tetraacetic acid (a chelating agent) | 0.10 |
| 1 | polyethylene glycol-75 lanolin | 1.20 |
| 1 | cocoamphocarboxyglycinate | 0.50 |
| 2 | propylene glycol | 2.00 |
| 2 | methylparaben | 0.10 |
| 2 | propylparaben | 0.05 |
| 2 | butylparaben | 0.05 |
| 3 | polysorbate 20 | 0.825 |
| 3 | fragrance | 0.45 |
| 4 | water | 60.00 |

After a brief untensioned period of, for example, up to about 30 seconds, e.g., about 3 to 20 seconds, in the holding box 42, the composite elastic material 40 is withdrawn therefrom. The provision of the holding box 42 or an equivalent structure allows the untensioned heat-bonded composite elastic material 40 to stabilize, that is cool, while it is in an untensioned arrangement. This allows the elastic sheet 12 to contract and gather the gatherable web immediately after bonding of the webs to each other. Additionally, this allows the elastic sheet 12 to cool in a relaxed, that is nontensioned, condition which avoids the elastic web becoming set at the stretched dimensions which it had assumed during bonding. If the elastic sheet 12 were to set in the tensioned state it would be unable to contract and form the generally parallel gathers in the non-elastic webs 32 and 36. Accordingly, the composite material 40 would not possess elasticity because any significant stretching of the composite would result in tearing of the non-elastic webs 32 and 36.

Upon leaving the holding box 42 the composite elastic material 40 passes through a nip 46 formed by two nip rollers 48 and 50. The nip rollers 48 and 50 serve to squeeze excess liquid 44 from the composite material 40. Alternatively, precise amounts of the liquid 44 may be applied by spraying as at a conventional spraying station 52.

Next, the composite material 40 is passed through the nip of nip rollers 48' and 50' to a conventional folding, interleaving and cutting station 54 where the composite material 40 is formed into a stack 56 of individual interleaved wet wipes 58. Then the stack 56 of interleaved wipes 58 is passed to a conventional boxing station 60 where the stack 56 is boxed as at 62. As is conventional, the box 62 may be provided with an arrangement to form a dispensing orifice therein.

Conventional drive means and other conventional devices which may be utilized in conjunction with the apparatus of FIG. 1 are well known and, for purposes of clarity, have not been illustrated in the schematic view of FIG. 1.

Figure 3:
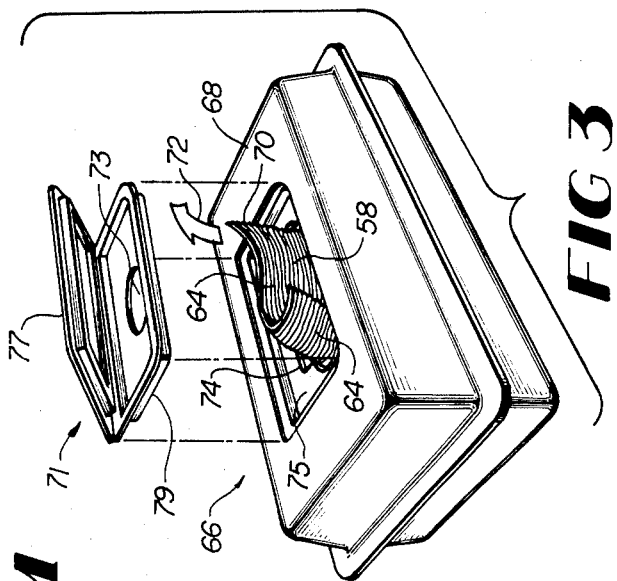
FIG. 3 is a perspective illustration of a wipe dispensing arrangement in accordance with the present invention.
Figure 2:
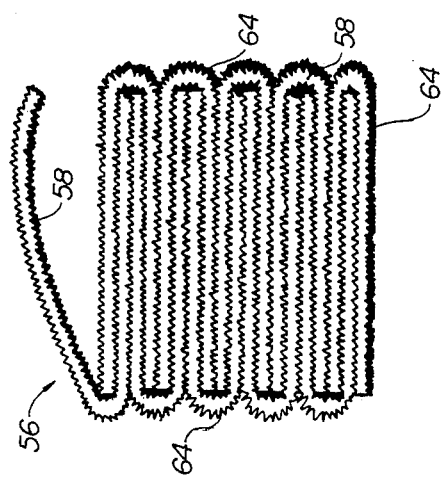
FIG. 2 is a schematic cross-sectional representation of a stack of wipes interleaved in accordance with the preferred embodiment of the present invention.

Preferably, the wet wipes 58 are interleaved so that the generally parallel gathers 64 on the surface of adjacent wipes 58 are in facing parallel arrangement. This configuration, which is schematically illustrated by FIG. 2, enables the generally parallel gathers 64 of adjacent wipes 58 to temporarily engage each other when a leading wipe is removed from the stack 56. This parallel configuration aids in assuring that the wipes will readily and easily dispense and that the next wipe will partially dispense and be available for later dispensation. Yet another advantage of interleaving the wipes 58 so that the generally parallel gathers 64 of adjacent wipes 58 are arranged in a parallel facing configuration is that such a configuration results in the direction of elasticity of the wipes 58 which is generally perpendicular to the gathers 64 being generally aligned with an idealized direction of removal of the wipes 58 from a dispenser. This is illustrated in FIG. 3 which shows a dispensing arrangement 66 that includes a container 68 which contains a stack 56 of interleaved individual wet wipes 58, and a user's hand (not shown) is withdrawing the leading wipe 70 in the idealized direction represented by the arrow 72. Because the direction of elasticity of the wipes 56 will be generally aligned with the idealized direction of removal 72 of the wipes 56, upon removal of a wipe 58 from the container 68 through a dispensing orifice 74 (which may have been formed by the prior removal of a portion of the container 68), the wipe 58 will tend to stretch slightly and snap into the user's hand. This snapping gives the user a positive indication of wipe removal without having to view the dispensing arrangement 66. The dispensing arrangement 66 may also include a hinged top portion 71 including a lower lid 79 having a dispensing orifice 73 which is smaller than the orifice 74 of the container 68. The hinged top portion 71 is adapted to sit into a recessed area 75 which surrounds the orifice 74 in the top of the container 68 so that a single wipe 58 may be withdrawn through the orifice 73 upon lifting the upper lid 77 of the top portion 71. Alternatively, if a user wishes to dispense a large number of wipes 58 the entire top portion 71 can be lifted from the recessed area 75 and a quantity of the wipes 58 may easily be withdrawn through the orifice 74.

Figure 4:
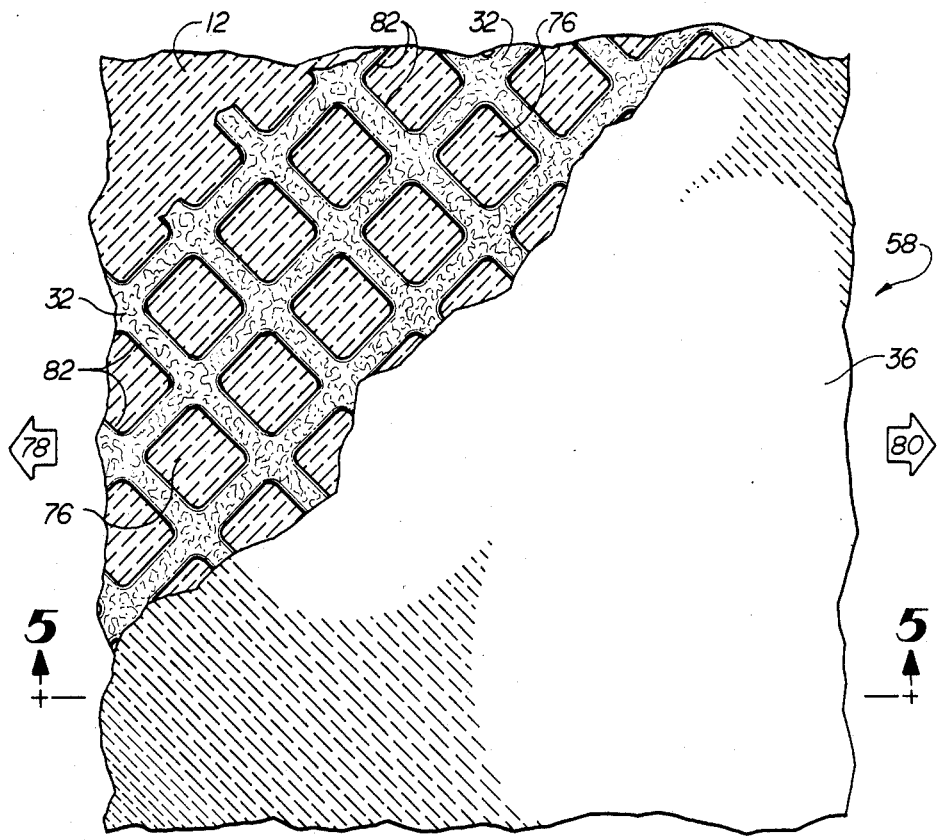
FIG. 4 is a planar view with portions cut away of a wipe in stretched condition.
Figure 5:
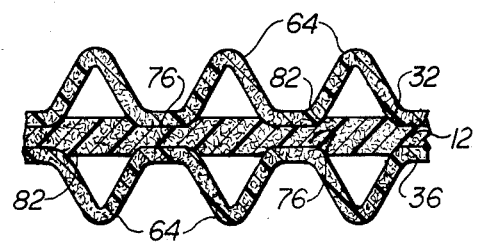
FIG. 5 is a cross-section of the wipe of FIG. 4 taken along line 5—5 of FIG. 4 with the wipe having been relaxed to illustrate the gathers.

For purposes of clarity FIG. 4 illustrates a portion of an elastic wet wipe 58 in stretched configuration to better illustrate the bonding pattern utilized thereon. The wet wipe 58 as illustrated in FIG. 3 has had a portion of the first non-elastic web 32 removed to reveal the elastic sheet 12 and the second non-elastic web 36. The wet wipe 58 includes a first non-elastic web 32 and a second non-elastic web 36 heat-bonded to respective opposite sides of an elastic sheet 12. Because the bond sites 76 are spaced-apart, generally parallel gathers or pleats 64 are formed in the webs 32 and 36 when the wet wipe 58 is in a relaxed condition as shown in FIG. 5 which is a cross-sectional view of the wipe 58 of FIG. 4 taken along line 5—5. The gathers 64 are not shown in FIG. 4 because the wipe 58 is in a stretched condition due to application of tensioning force in the directions of arrows 78 and 80. FIG. 5 illustrates that the wet wipe 58 has a plurality of embossed bond sites 76 formed by the action of the raised portions of the embossing calender roller 28 in cooperation with the anvil roller 30. The temperature and pressure maintained in the nip 24 between the calender roller 28 and the anvil roller 30 was such that the pressure and temperature imposed by the raised portions of the calender roller 28 formed indentations within the elastic sheet 12 by softening or melting the portions of the sheet 12. The peripheral portions 82 of the indentations of the sheet 12 include a resolidified portion of the material which was formerly located in the indented area. The peripheral portions 82, upon resolidification after their softening or melting in the pressure nip 24 of calender roller 28 and anvil roller 30, tend to form a reasonably strong bond with the overlaid non-elastic webs 32 and 36.

Comparative testing of the dispensing reliability of the wet wipes 58 and the dispensing arrangement 66 of the present invention as compared to another dispensing arrangement was conducted. The other comparative dispensing arrangement was a two layered material having an air formed cellulosic web laminated to a spunbonded polypropylene web by an adhesive. The air formed web may be obtained from James River Corporation under the trade designation SC 130HB had a basis weight of about 30 pounds per ream (3,000 square feet). Because neither of these webs were elastic the two layer web was not stretch-bonded. The composite sample material is more clearly defined in a presently pending, commonly assigned, application entitled "Two-sided, Composite Wipe Having Improved Softness and Strength" to Hoffman, Kerch and Bohmer. This application was filed on Feb. 5, 1986 and has a Ser. No. of 06/826,708. The wipes of the present invention were formed from a palindromic three layer stretch-bonded laminate having two outer layers formed from a spunbonded polypropylene web (about 12.5 grams per square meter basis weight) and an inner layer formed from a meltblown web (about 37 grams per square meter basis weight) of Exxon Escorene LD 764 (077.004). The laminate had an elasticity of about 40 percent in the machine direction. The parameters of the test were that these two materials were each formed into thirty (30) stacks of interleaved wipes with each stack having eighty (80) individual wipes. The wipes of the present invention were interleaved with the generally parallel gathers of adjacent wipes being aligned in generally parallel configuration. The withdrawal reliability and the force necessary to withdraw a wipe were then measured with various amounts of the liquid described in Table I being present in the stretch-bonded laminate wipe of the present invention and with the same liquid also being present in the air formed comparative sample with the exception that the liquid present in the comparative sample contained only 0.50 percent, by weight, of the polysorbate 20 and only 0.125 percent, by weight, of the fragrance. Otherwise, the two liquids were substantially identical.

The results of this test are detailed below in Table II.

TABLE II

| | DISPENSING RELIABILITY | |
|---|---|---|
| Moisture[1] | Withdrawal Reliability[2] | Withdrawal Force[3] |
| (a) Comparative Example | | |
| 105 | 93.1 | 94 |
| 130 | 85.1 | 149 |
| 166 | 75.4 | 422 |
| 259 | 16.0 | 718 |
| (b) Present Stretch-Bonded Laminate Wipe | | |
| 60 | 95.7 | 104 |
| 133 | 99.7 | 129 |
| 145 | 99.4 | 271 |
| 205 | 88.4 | 342 |

[1] = percent, by weight, moisture present in wipe as a percent of its dry weight
[2] = percent of wipes dispensing correctly
[3] = measured in grams per wipe. (The force in grams necessary to withdraw a wipe from a stack.)

This data demonstrates a strong correlation between dispensing reliability and percent moisture (liquid) present in that, generally speaking, dispensing reliability tends to decrease as moisture content increases. The improved dispensing reliability of the wipes of the present invention is clearly apparent in that at 133 percent moisture content the present wipes have a dispensing reliability of 99.7 percent, whereas at 130 percent moisture content the other wipes have a dispensing reliability of only 85.1 percent.

An interesting observation that has been made is that the effect of gravity on the liquid contained within the present wipes appears to be significantly less than its effect on prior wipes of cellulosic materials. That is, seepage of the liquid to the bottom of a stack of the present wipes is far less rapid than seepage which has been associated with cellulosic wipes. It has been hypothesized that the lower rate of seepage of the present wipe is due to the fact that the meltblown and/or spunbonded fibers of the present wipe are not subject to capillary collapse as is believed to be the case with cellulosic materials.

It is to be understood that the above disclosure of the presently preferred embodiment of the invention is to be taken as illustrative of the invention. Further, it is clear that, in view of the present disclosure, those of skill in the art should be capable of making numerous modifications without departing from the true spirit and scope of the invention. For example, different combinations of non-elastic webs and elastic sheets could be stretch-bonded together and the elastic sheet could be stretched, by conventional arrangement, in more than one direction.

What is claimed is:

1. A wet wipe which is elastic in at least one direction, said wet wipe comprising:
   an elastic sheet;
   at least one non-elastic non-woven web joined to said elastic sheet at least at two areas, said non-elastic web being gathered between said two areas; and
   a liquid distributed within at least one of said sheet and said web.

2. The wet wipe of claim 1, wherein said liquid consists of at least one material selected from the group of materials including preservatives, fragrances, emollients, humectants, detergents and soaps.

3. The wet wipe of claim 1, wherein said elastic sheet is an elastic non-woven web of meltblown fibers and the non-elastic web is a web of spunbonded fibers.

4. The wet wipe of claim 3, wherein said meltblown fibers are comprised of ethylene vinyl acetate and said spunbonded fibers are comprised of polypropylene.

5. The wet wipe of claim 4, wherein said liquid consists of at least one material selected from the group of materials including preservatives, fragrances, emollients, humectants, detergents and soaps.

6. The wet wipe of claim 4, wherein the basis weight of the polypropylene web is from about 10 to about 30 grams per square meter.

7. The wet wipe of claim 4, wherein the basis weight of the elastic nonwoven web is from about 30 grams per square meter to about 50 grams per square meter.

8. The wet wipe of claim 4, wherein said ethylene vinyl acetate comprises from about 10 percent, by weight, to about 50 percent, by weight, of vinyl acetate monomer.

9. The wet wipe of claim 4, wherein said meltblown fibers are meltblown microfibers.

10. The wet wipe of claim 4, wherein said spunbonded fibers are spunbonded microfibers.

11. The wet wipe of claim 4, wherein said polypropylene has a polydispersity of from about 1 to about 5.

12. The wet wipe of claim 11, wherein said polypropylene has a melt flow of about 35 grams per 10 minutes when measured in accordance with ASTM D 1238 at 230 degrees C. and under a 2,160 gram load.

13. The wet wipe of claim 8, wherein said ethylene vinyl acetate comprises about 26 percent, by weight, to about 30 percent, by weight, of vinyl acetate monomer and has a melt flow of about 180 grams per 10 minutes when measured in accordance with ASTM D 1238 at 190 degrees C. and under a 2,160 gram load.

14. A palindromic stretch-bonded elastic wet wipe adapted to stretch from at least about 30 percent to about 50 percent in at least one direction, said wipe comprising:
   an inner elastic nonwoven web having a basis weight of from about 35 grams per square meter to about 40 grams per square meter, said elastic web comprising meltblown microfibers of ethylene vinyl acetate having from about 26 percent, by weight, to about 30 percent, by weight, of vinyl acetate monomer and a melt flow rate of about 180 grams per 10 minutes when measured in accordance with ASTM D 1238 at 190 degrees C. and under a 2,160 gram load;
   two outer non-elastic nonwoven webs having a basis weight of from about 10 grams per square meter to about 20 grams per square meter, said non-elastic webs comprising spunbonded microfibers of polypropylene having a polydispersity of from about 1 to about 5 and a melt flow rate of about 35 grams per 10 minutes when measured in accordance with ASTM D 1238 at 230 degrees C. and under a 2,160 gram load; and
   from about 80 percent, by weight, to about 160 percent, by weight, based on the combined weight of the elastic and non-elastic webs, of a liquid comprising at least one material selected from the group of materials consisting of fragrances, preservatives, soaps, humectants and emollients.

15. A stretch-bonded palindromic elastic nonwoven wet wipe adapted to stretch at least about 40 percent in at least one direction, said wipe consisting essentially of:
   an inner elastic nonwoven web of meltblown ethylene vinyl acetate microfibers, said elastic web having a basis weight of about 37 grams per square meter;
   two outer nonwoven non-elastic webs of spunbonded polypropylene microfibers bound to said elastic web by thermal pin embossment, said non-elastic webs each having a basis weight of about 12.5 grams per square meter; and
   about 120 percent, by weight, based on the combined weight of the elastic and non-elastic webs, of a liquid consisting essentially of about 94.475 percent, by weight, of water; about 0.20 percent, by weight, of benzalkonium chloride; about 0.10 percent, by weight, of citric acid; about 0.60 percent, by weight, of disodium phosphate; about 0.10 percent, by weight, of trisodium ethylene diamine tetraacetic acid; about 1.20 percent, by weight, of polyethylene glycol-75 lanolin; about 0.50 percent, by weight, of cocoamphocarboxyglycinate; about 2.00 percent, by weight, of propylene glycol; about 0.10 percent, by weight, of methylparaben; about 0.05 percent, by weight, of propylparaben; about 0.05 percent, by weight, of butylparaben; about 0.825 percent, by weight, of polysorbate 20 and about 0.45 percent, by weight, of a fragrance
wherein the ethylene vinyl acetate copolymer of the elastic web has about 28 percent, by weight, of vinyl acetate monomer and a melt flow rate of about 180 grams per 10 minutes when measured in accordance with ASTM D 1238 at 190 degrees C. when under a 2,160 gram load and the polypropylene of the non-elastic webs has a polydispersity of about 4.5 and a melt flow rate of about 35 grams per 10 minutes when measured in accordance with ASTM D 1238 at 230 degrees C. and under a 2,160 gram load.

* * * * *

UNITED STATES PATENT AND TRADEMARK OFFICE
CERTIFICATE OF CORRECTION

PATENT NO. : 4,741,944
DATED : May 3, 1988
INVENTOR(S) : David M. Jackson

It is certified that error appears in the above—identified patent and that said Letters Patent is hereby corrected as shown below:

On the Title Page:
  [75] delete "William H. Vogler" as inventor

Signed and Sealed this

Eighteenth Day of October, 1988

Attest:

DONALD J. QUIGG

*Attesting Officer*          *Commissioner of Patents and Trademarks*